(12) United States Patent
Klepel

(10) Patent No.: US 9,009,097 B2
(45) Date of Patent: Apr. 14, 2015

(54) IDENTIFICATION OF SUBSTANCES BY ION MOBILITY SPECTROMETRY

(75) Inventor: Stefan Klepel, Tauche (DE)

(73) Assignee: Bruker Daltonik GmbH, Bremen (DE)

( * ) Notice: Subject to any disclaimer, the term of this patent is extended or adjusted under 35 U.S.C. 154(b) by 725 days.

(21) Appl. No.: 13/077,194

(22) Filed: Mar. 31, 2011

(65) Prior Publication Data

US 2011/0246414 A1 Oct. 6, 2011

(30) Foreign Application Priority Data

Mar. 31, 2010 (DE) .......................... 10 2010 013 548

(51) Int. Cl.
*G06N 5/00* (2006.01)
*G01N 27/62* (2006.01)
*G06N 5/02* (2006.01)

(52) U.S. Cl.
CPC ............... *G01N 27/622* (2013.01); *G06N 5/02* (2013.01)

(58) Field of Classification Search
CPC ............................... G06N 5/02; G01N 27/622
USPC .......................................................... 706/54
See application file for complete search history.

(56) References Cited

U.S. PATENT DOCUMENTS

| | | | |
|---|---|---|---|
| 7,541,577 | B2 | 6/2009 | Davenport et al. |
| 2005/0133710 | A1 | 6/2005 | Losch et al. |
| 2011/0042559 | A1 | 2/2011 | Klepel |

OTHER PUBLICATIONS

Bell et al., "Classification of ion mobility spectra by functional groups using neural networks", Analytica Chimica Acta, vol. 394, 1999, pp. 121-133.
Eiceman, "Ion-mobility spectrometry as a fast monitor of chemical composition", Trac, Trends in Analytical Chemistry, Elsevier, Amsterdam, NL, vol. 21, No. 4, 2002, pp. 259-275.
Eiceman et al., "Pattern recognition analysis of differential mobility spectra with classification by chemical family", Analytica Chimica Acta, Elsevier, Amsterdam, NL, vol. 579, No. 1, 2006, pp. 1-10.
Chen et al., "Real-time two-dimensional wavelet compression and its application to real-time modeling of ion mobility data", Analytica Chimica Acta, Elsevier, Amsterdam, NL, vol. 490, No. 1-2, 2003 pp. 59-69.

*Primary Examiner* — Lut Wong
(74) *Attorney, Agent, or Firm* — O'Shea Getz P.C.

(57) ABSTRACT

The invention relates to identifying substances in a sample by similarity comparisons between series of ion mobility spectra of the sample and series of ion mobility spectra of reference samples. The collection of series of spectra of reference samples, termed reference library, are divided into classes, with the class assignment of a series of spectra being calculated from the measured values themselves, and limiting the similarity comparisons to series of spectra with the same class assignment. First and second moments of the spectra have proven to be particularly favorable characteristics for the class assignment.

8 Claims, 5 Drawing Sheets

IDENTIFICATION OF SUBSTANCES BY ION MOBILITY SPECTROMETRY

PRIORITY INFORMATION

This patent application claims priority from German Patent Application 10 2010 013 548.8 filed on Mar. 31, 2010, which is hereby incorporated by reference.

FIELD OF THE INVENTION

The invention relates to ion mobility spectrometry, and in particular to identifying substances in a sample by similarity comparisons between a series of ion mobility spectra of the sample and series of ion mobility spectra of reference samples.

BACKGROUND OF THE INVENTION

In a commonly used ion mobility spectrometer, ions are generated in an ion source and then introduced into a drift region of the spectrometer by a gating grid over a short period of time. An axial electric field pulls the ions of these ion pulses through a stationary drift gas in the drift region, their velocity being determined by their "mobility". At the end of the drift region, the incident ion current is measured at an ion detector, digitized and stored as a "mobility spectrum" in the form of a sequence of digitized ion current values. This series of ion current values is usually converted into a peak list, which contains only the drift times of the peaks and their peak heights.

In the ion source of an ion mobility spectrometer, several ion species such as monomer ions, dimer ions, dissociative ions and associative ions are usually formed from the molecules of one substance. Some substances even form ions of greater complexity. The number of ions formed can be further increased by the addition of doping agents. The ions of the substances are usually formed by so-called "chemical ionization at atmospheric pressure" (APCI) in reactions with reactant ions, usually by protonation or deprotonation of the substance molecules or by electron transfer or ion attachment. The reactant ions are usually generated in the ion source by irradiating the carrier gas with ionizing radiation. The intensity ratios of the individual ion species with respect to each other depend on the concentration of the analyte molecules and on their affinity for the different types of charge transfer in the ion source.

The mobility of the ions can be used for the identification of a substance, the mobility of the main signal, usually the monomer ion, being the one which is often used. The identification can be confirmed by the mobility of a secondary signal, usually of the dimer ion or a dissociation ion. Usually, both positive and negative ions can be measured in mobility spectrometers by switching over the voltage. For some substances, both positive and negative ions are formed; the mobilities of the ions of the other polarity can then be used to confirm the identity.

The mobility values of the relevant signals of known harmful substances, or even their full mobility spectra, are stored in corresponding data collections, which are termed libraries, or more precisely reference libraries. The diffusion broadening of the mobility signals limits the mobility resolution, while the low stability of the pressure and temperature sensors, whose measurements are required to calculate normalized mobilities, limit the accuracy of the mobility determination. Consequently, comparisons with mobility values in libraries must be performed with relatively large tolerances, which amount to at least around one percent of the mobility value; the small number of peaks and the low mobility accuracy mean that reliable identification is not always guaranteed.

This method of identification is quite successful if the types of harmful substance which can occur are severely limited in number and rarely suffer from interferences with other substances. This is the case with the analysis of military warfare agents, for example. In other application fields, such as the testing of suitcases for adherent traces of explosives, however, this type of identification is not sufficient because a large number of substances can interfere with the measurement.

As an example, FIGS. 7 and 8 show the series of spectra of a sample named "SPICE" and the explosive "TNT". If one compares only two characteristic mobility spectra from this, as is shown in FIG. 9, they are almost identical, although the series of spectra as a whole look very different.

The detection of explosives on site (e.g., on suitcases at airports) is therefore a particular challenge. The usual procedure is to take swab samples from the outside of the suitcases and vaporize them at the entrance of the ion source of the mobility spectrometer. The problem is that the measurements are frequently disturbed by other substances in the suitcases, such as essential oils from perfumes, talcum powders, soaps or spices, which often cause a false alarm because they generate ions of the same mobility as the target substances, as is depicted in FIG. 9. A large number of false alarms lead to a rejection of the method.

The identification can be improved if rather than just individual ion mobility spectra complete series of spectra are acquired, the analytes introduced as vapor pulses, whereby the concentration of the analytes in the ion source passes through an ascending and descending curve. The measured data of a series of spectra are arranged along two axis, a sample axis (related to the sequence of spectra) and a mobility axis (related to a single ion mobility spectrum, also often termed as drift time axis). As can been seen in FIGS. 7 and 8, the sample axis is a "slow axis" with a range of tens of seconds, whereas the mobility axis is a "fast axis" with a range of tens of milliseconds. A method of this type is disclosed in U.S. Published Application No. 20110042559 (S. Klepel). Since the formation of the different ion species of a substance under analysis depends on their concentration in the ion source, a series of ion mobility spectra is acquired, in which the spectra change greatly from another along the sample axis. The information content of such a series of spectra is by far greater than that of an individual mobility spectrum, but the evaluation of the information, which is done by similarity comparisons with series of reference spectra from a library, is much more difficult.

U.S. Pat. No. 7,541,577 also discloses an identification method which is based on series of spectra and is also particularly suitable for explosives. A so-called "peak shifting" of the mobility signals in a series of mobility spectra, i.e., variabilities of the mobility of the ions formed, is used for an identification. The variabilities are attributed to nonlinear and concentration-dependent behavior in the presence of labeling substances ("taggants"), which must be present in the explosives.

When the terms "spectra", "mobility spectra" and "series of spectra" are used below, they refer to "ion mobility spectra" or "series of ion mobility spectra" unless specifically indicated otherwise. The spectra or series of spectra can have been measured using a drift region ion mobility spectrometer described above, and also with other types of mobility spectrometer.

There is a need to increase the certainty of identification for substances under analysis, particularly explosives, by evaluating series of ion mobility spectra. At the same time, the extent of the information processing is to be kept to an acceptably low level so that it is also possible to carry out identifications with relatively a simple instrument and a processor/computer in a relatively rapid sequence.

SUMMARY OF THE INVENTION

A method for identifying substances in a sample comprises automatic similarity comparisons between a sample series of ion mobility spectra of the sample and multiple reference series of ion mobility spectra of reference substances stored in a reference library. A series of ion mobility spectra are acquired, both for samples to be analyzed and for samples of reference substances. The reference library may be stored in a reference library associated with a processor/computer.

Any collection of series of ion mobility spectra of known reference substances and their mixtures shall be included here in the term "reference library".

The reference library may be divided into classes in order to shorten the time needed for the similarity comparisons, and in particular to increase the certainty of identification. The sample series is assigned to one of these classes and may be compared only with those reference series of the reference library that have the class assignment of the sample series, optionally also with reference series from a neighboring class, especially if the sample series is located close to the boundary of the class it is assigned to. It is particularly preferable if the assignment of a series to a class is determined from measured values of the ion mobility spectra.

A measurement comprises the acquisition of a series of spectra with an ion mobility spectrometer. The series starts before the substance is introduced and ends after the introduction of the substance has been completed, preferably when the mobility spectra again show the initial state of the ion mobility spectrometer. The ion mobility spectra change across the series of spectra. The ion mobility spectra depend on the quantity of the respective substance introduced, up to a substance-specific saturation.

The division of the reference library into classes is preferably based on characteristics of the individual mobility spectra, which may be computed for each ion mobility spectrum, like spectrum moments along the drift axis. The first moment (spectrum center; sometimes termed "centroid") and the second central moment (variance) of an ion mobility spectrum have proven to be particularly favorable characteristics; and it has been shown that the maximum value of spectrum center of a series of spectra along the sample time reflects the quantity of substance introduced quite well as long as the ion mobility spectrometer is not saturated.

The maxima of characteristics determined from each ion mobility spectrum of a series along the sample axis may be used to determine the assignment of the series of spectra to a class. For the purpose of dividing the reference library into classes it has been proven to be advantageous that the ranges covered by the respective maximum values of the characteristics across all series are divided into intervals and that the classes of the reference library are related to these intervals. A particular advantageous division results when the intervals are equal in size. When two different types of characteristics are used, a two-dimensional class division results. Beside of the maximum values of the spectrum moments, the curve of the spectrum moments along the sample axis itself may be analyzed and coefficients of the analysis may be used as characteristics or to determine characteristics, i.e., that the analysis of the curve of a certain spectrum moment along the sample axis can result in multiple classes due to the plurality of different coefficients. The curve of the spectrum moments are preferably analyzed by at least one of (i) method of moments (moments of curves along the sample axis), (ii) Taylor expansion, (iii) Fourier transform and (iv) Wavelet transform.

As has already been noted above, the spectrum center approximately represents the quantity of substance introduced. Since this quantity has a strong influence on the form of the ion mobility spectra, it is advantageous to store a large number of series of spectra for each reference substance in the reference library, the series of spectra being based on the introduction of different quantities of the reference substance. On the other hand this means, however, that several series of spectra of one reference substance can accumulate in one class, which is not advantageous for the similarity comparison.

The computational effort required for the similarity comparisons may be reduced again by storing only one, idealized series of spectra for each reference substance in any class of the reference library, the series having been obtained from one or more real (measured) series of spectra of the reference substance. The idealized series of spectra can, for example, be obtained by only including those mobility spectra which give a smooth curve of one of the characteristics, preferably a smooth curve of the spectrum center. For example, the aim should be to obtain a smooth curve of the spectrum center from zero to the maximum value and back to zero. The similarity comparison between series of ion mobility spectra of the sample (sample series) with series of ion mobility spectra from reference substances (reference series) from one class of the reference library can then be performed by comparing those ion mobility spectra of the sample series and the reference series which have the same spectrum center. In particular, ion mobility spectra with the same spectrum center in the ascending curve or with the same spectrum center in the descending curve should be compared.

It may happen that for a mobility spectrum of the sample no suitable mobility spectrum with the same spectrum center is available in the idealized reference series of the reference library. In this case, a suitable mobility spectrum for the similarity comparison can be obtained by interpolation from adjacent mobility spectra of the idealized reference series or the measured sample series.

The processing of measured data preferably runs automatically via executable program instructions in a processor/computer device. An ion mobility spectrometer is usually equipped with a computer, and the computer may store and execute the program instructions and have access to a reference library which is divided into classes.

These and other objects, features and advantages of the present invention will become more apparent in light of the following detailed description of preferred embodiments thereof, as illustrated in the accompanying figures.

DETAILED DESCRIPTION OF THE INVENTION

Figure 1:
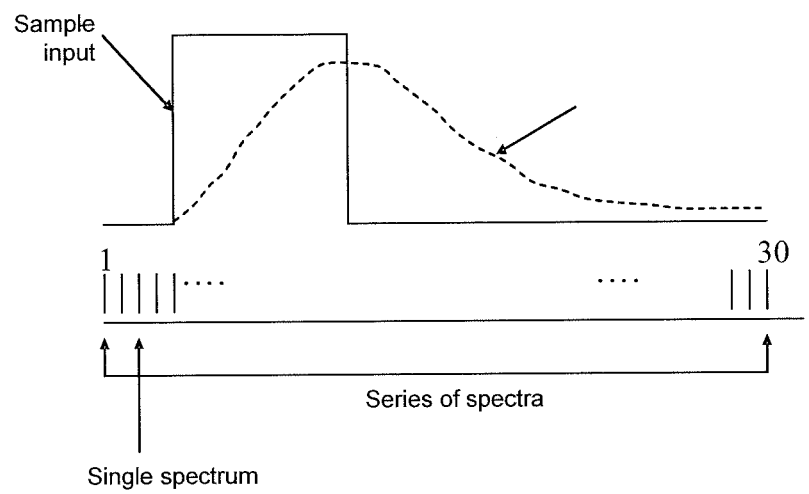
FIG. 1 is a schematic representation to define the measurement of a series of spectra.
Figure 2:
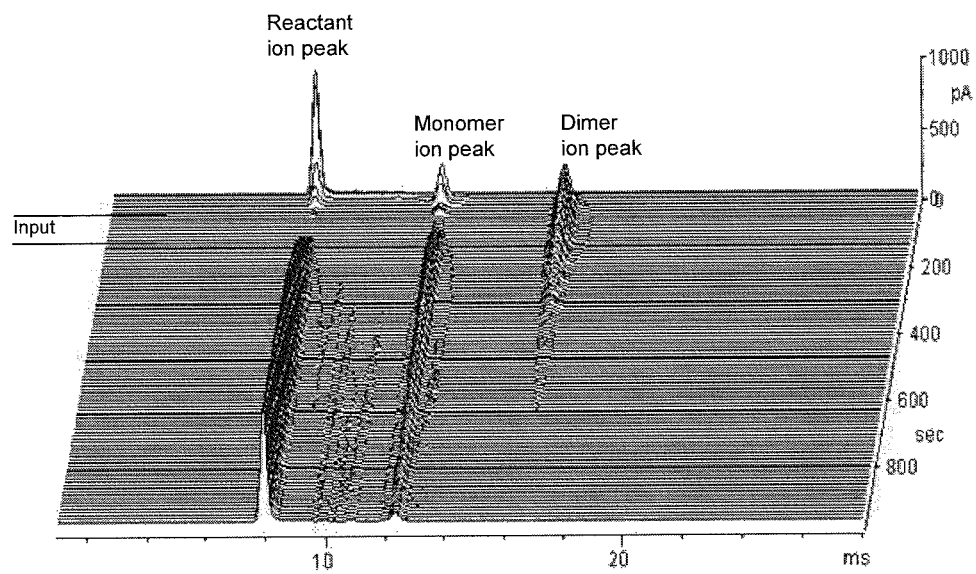
FIG. 2 is a representation of a series of spectra of DPM.

A "measurement" involves the acquisition of a series of spectra with an ion mobility spectrometer, e.g., with a short pulsed, introduction of the sample. The measurement of a series of spectra should start before the sample is introduced and ends after the introduction of the sample has been completed, preferably when the mobility spectra again indicate the initial state of the spectrometer before the sample was introduced, as is schematically depicted in FIG. 1. An example of a series of spectra measured in this way is shown in FIG. 2, where the substance measured is dipropylene glycol monomethyl ether (DPM). A clean mobility spectrometer provides a mobility spectrum which essentially only includes the peaks of the reactant ions. The reactant ions serve to chemically ionize the substances introduced, as the specialist is aware and as has been described above.

As can be seen from FIGS. 1 and 2, each "series of spectra" includes a sequence of individual mobility spectra. A mobility spectrum can, in turn, be composed of individual mobility spectra added together. A series of spectra may, for example, contain 60 mobility spectra, each corresponding to a one (1) second duration on the sample axis, but where each of these mobility spectra was obtained from 30 individual mobility spectra, each of 33 milliseconds duration. There are also other ways of acquiring mobility spectra, however, but usually each mobility spectrum is averaged over a time interval in the order of one second.

The mobility spectra, which includes a sequence of measured and digitized values for the ion current, can be transferred, after the measurement, into a peak list by one of the known peak-detection programs, with the drift times of the peaks and their peak heights being listed in this peak list. The mobility spectra can be corrected by subtracting the background. When the term "mobility spectrum" is used below, it usually can be taken to mean the peak list. Additional information may be attached to these peak lists.

The sample from which the series of spectra is obtained can be an "analysis sample" containing one or more unknown substances to be identified, in which case "series of analyte spectra" (sample series) are measured; but it can also be a "reference sample" containing one or more known "reference substances", in which case "series of reference spectra" (reference series) are then generated. The inclusion of series of spectra of frequently occurring mixtures of reference substances in the reference library helps to make identifications unambiguous. Mobility spectra change greatly across a series of spectra, as can be seen from the example in FIG. 2. However, all mobility spectra of complete series of spectra are particularly dependent on the quantity of the substances in the samples introduced in each case for the measurement of the series of spectra. It is therefore only possible to compare mobility spectra from series of spectra derived from measurements made with the same quantity of substance in the analyzed samples and reference samples. For the unknown substances being analyzed, however, the quantity introduced is usually unknown.

The identification by similarity comparison of series of ion mobility spectra of the analytical sample may be performed with series of ion mobility spectra of a reference library. Similarity comparison involves the calculation of similarity indices between a sample series of mobility spectra of the analytical sample and reference series of mobility spectra in the reference library. The specialist is aware of many different forms of algorithm for such similarity comparisons; many substance identifications in other areas are also usually based on similarity comparisons between analytical spectra and reference spectra from reference libraries, be they mass spectra, infrared spectra, nuclear resonance spectra or others. In these cases also, the similarity comparisons are usually based on the calculation of similarity indices; in high-resolution spectroscopy, a correct identification is assumed if the similarity index exceeds a threshold value and has a minimum difference to the spectrum with the next closest similarity, for example. The low-resolution character of ion mobility spectra means a simple identification which relates to only one single spectrum is not possible here; a definite identification therefore requires that similarity indices for all ion mobility spectra in a series are calculated in some way. In an embodiment of the similarity comparison, the similarity indices can be derived for one series of spectra overall in a single calculation, or separately for many individual mobility spectra of the series of spectra, in which case the similarity indices for the individual mobility spectra are then summarized (or averaged) to give a similarity index for the series of spectra. In another embodiment of the similarity comparison, one or more intervals along the mobility axis are selected and only these selected parts of the sample series and the reference series are compared in the similarity comparison. If multiple series of the same reference substance are repeatedly measured, peaks which appear with high probability in the multiple series can be marked as characteristic peaks and used to select the intervals of interest. The similarity comparison in a region of interest can for example be performed by determining the curve of the center of a characteristic peak along the sample axis in the reference series and correlating this curve with the respective curve in the sample series. To identify a substance in a mixture of substances, the similarity indices of those reference series which show a sufficient match with the sample series can be weighted, for example by known detection limit of the corresponding reference substance(s) or by predetermined rules, to generate a new list of best matches. The predetermined rules may comprise knowledge about suppression effects of substances against other substances in the ionization process of the ion source.

The reference libraries may contain for example series of spectra of hundreds or thousands of reference substances, and for each reference substance there can be many series of spectra, measured by introducing different quantities of sample (e.g., using dilution series). The similarity comparisons therefore take up a lot of data processing time if all the series of spectra in the reference library have to be used for the comparison.

The reference library may be divided into classes to reduce the time needed for the similarity comparison, and in particular to also increase the certainty of identification. The similarity comparisons of ion mobility series of spectra of the analytical sample may only be performed with spectra from corresponding classes of the reference library.

Such a division into classes may depend on external measurement parameters, such as how the sample was obtained, the quantity of sample introduced, how the sample is introduced (e.g., temperature profile in the vaporizer of the ion mobility spectrometer), the chemical class of the samples to be analyzed, such as explosives or drugs, and other parameters. In one embodiment the assignment of a series of spectra to a class may not depend on external parameters and can be determined from the measured values of the series of spectra itself. Experimental conditions, like the temperature profile in the vaporizer, can be varied in an ion mobility spectrometer. Reference series can be acquired under different experimental conditions. The reference library may therefore also comprise different reference series for the same reference substance (including mixtures of different substances) acquired under different experimental conditions.

The division of the reference library into classes is, in detail, based on characteristics which can be easily computed from the ion mobility spectra in each case. "Spectrum moments", calculated analogously to mass moments of a system, have proven to be advantageous characteristics; particularly advantageous are the "spectrum center" (the first moment) and "second central moment of the spectrum" (the variance) of an ion mobility spectrum; it has been found that the maximum spectrum center of ion current of a series of spectra characterizes the quantity of substance introduced.

The first moment or "spectrum center" of a mobility spectrum is understood to be the drift time ts ($t_s = \Sigma(t_i \cdot h_i)/\Sigma(h_i)$), where $t_i$ is the drift time of the $i^{th}$ peak and $h_i$ its peak height. The summations extend over the peaks, i.e., over all i. This corresponds to deriving a center of mass for masses distributed along the axis t, but here it is not the masses of the ions but rather the size $h_i$ of the ion currents used in the calculations. The calculation is done from the peak list, which contains the values for $t_i$ and $h_i$.

In order to obtain positive values from zero upwards here, the position of the spectrum center can be referenced to the drift time $t_0$ of the reactant peak: $t_s - t_0$. To obtain at a dimensionless value, the "Z-value" ($Z = (t_s - t_0)/t_e$) is introduced, where $t_e$ is an arbitrary unit of time, a millisecond, for example. This Z-value thus corresponds to a position of the spectrum center which is shifted and normalized. The maximum of the Z-values of a series of spectra ($Z_{max}$) has proven to be a measure for the quantity of substance introduced, wherein the introduced quantity of a substance is approximately proportional to $\exp(Z_{max})$; dividing the library into Z-value classes is therefore particularly effective. For easier understanding, the term "spectrum center" is often retained below when the Z-value is meant.

Figure 3:
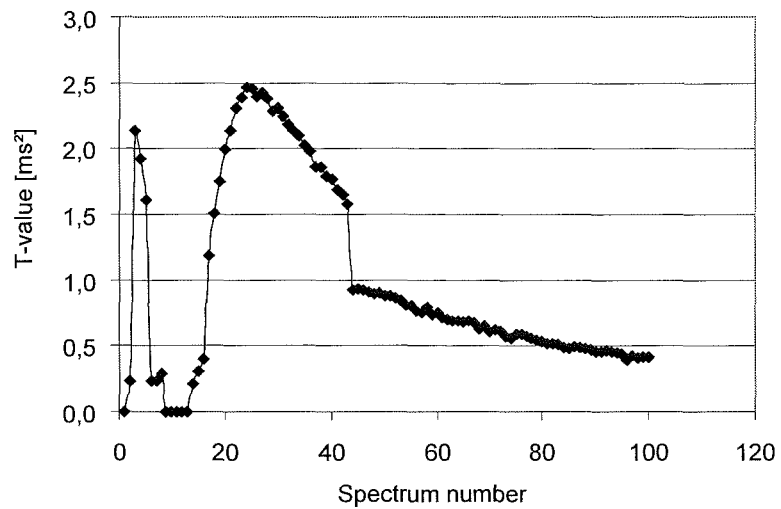
FIG. 3 is a characteristic plot of the T-value for the series of spectra in FIG. 2.

In analogy, the "second central moment" T of a mobility spectrum is defined as: $T = \Sigma((t_i - t_s)^2 \cdot h_i)$. This T-value (variance) essentially states how many larger peaks are present in the mobility spectrum and how far apart they are on the drift time axis. If a mobility spectrum includes only one single peak, the T-value is close to zero. FIG. 3 shows the characteristic of the T-values for the series of spectra of FIG. 2. The T-values of a series of spectra often form a complex curve because along the series of spectra, the formation of individual peaks alternates with the formation of substance conglomerates.

For the purpose of determining the assignment of a series of spectra to a class, the maxima of the characteristics of all ion mobility spectra of a series, e.g., $Z_{max}$ as the maximum Z-value and $T_{max}$ as the maximum T-value, can particularly be used. For the purpose of dividing the reference library into classes, it has proven advantageous to divide the ranges covered by the respective maxima $Z_{max}$ and $T_{max}$ of all series of spectra from the reference library into intervals in order to provide classes. A particularly advantageous division results when the intervals are chosen to be of equal size. When two different types of characteristics are used, a two-dimensional class division results. It is advantageous, for example, to divide the $Z_{max}$ range into for example about 15 proportions and the $T_{max}$ range into about 6 proportions. This results in about 90 classes. The series of spectra are stored in the classes of the reference library in the form of series of peak lists, which can be supplemented by T-values and Z-values.

As noted above, the maximum value of spectrum center $Z_{max}$ of a series of spectra approximately describes the quantity of substance introduced, and this quantity has a strong influence on the form of the ion mobility spectra. It is therefore advantageous to store a large number of series of spectra, measured by introducing different quantities of the reference substance, for each reference substance in the reference library. The different quantities for introduction can be produced by dilution series of dissolved substances, for example. The series of reference spectra thus measured are spread widely over different Z-classes, with only a narrow spread over the T-classes. Furthermore, it is advantageous to also include series of spectra of frequently occurring mixtures of reference substances in the reference library, because they increase the certainty of the identifications in many cases. Such mixtures of reference substances can be spices or perfumes, for example.

Figure 4:
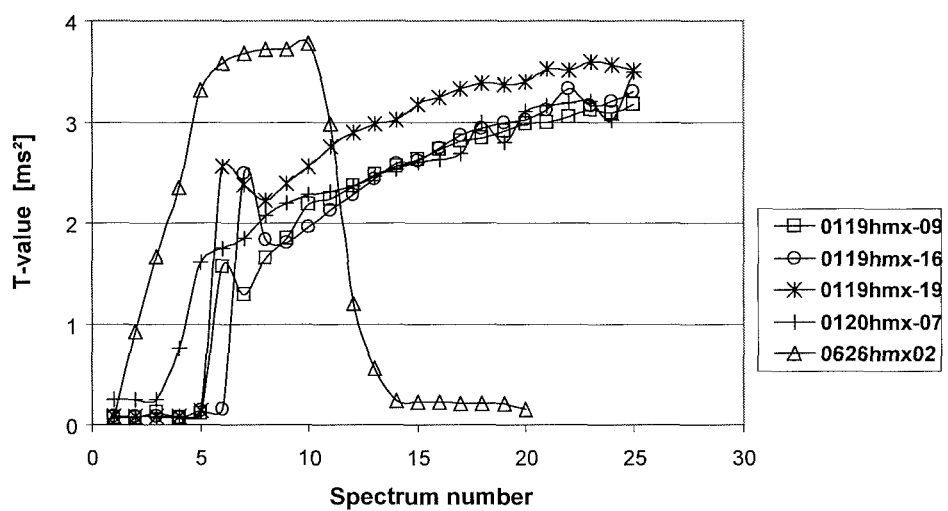
FIG. 4 is T-characteristic plots for 5 selected HMX series of spectra of one class.
Figure 5:
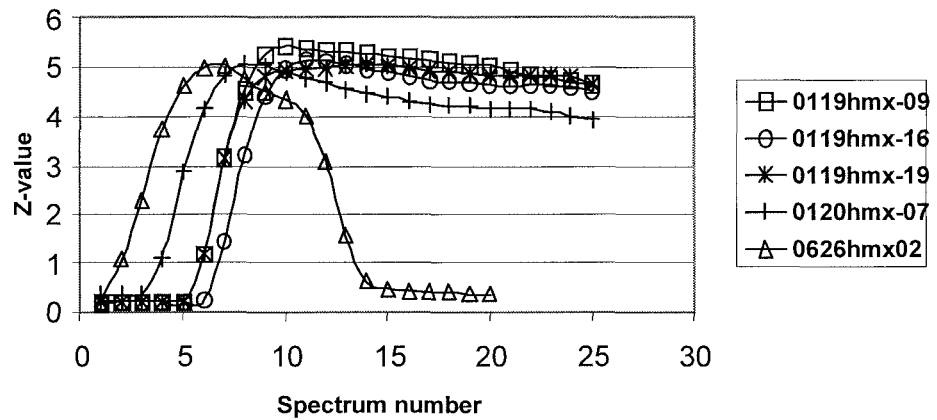
FIG. 5 is Z-characteristic plots for 5 selected HMX series of spectra of the same class as in FIG. 4.

It is also possible, however, that several series of spectra of a single reference substance can accumulate in one Z/T-class, which is not advantageous for the similarity comparison. FIGS. 4 and 5 depict the characteristics of the T-values and Z-values for several series of spectra of a reference substance (explosive HMX; cyclotetramethylene-tetranitramine) from one Z/T-class. It is particularly evident that the curves of the characteristics along the sample axis (and thus the series of spectra) are not very reproducible.

Figure 6:
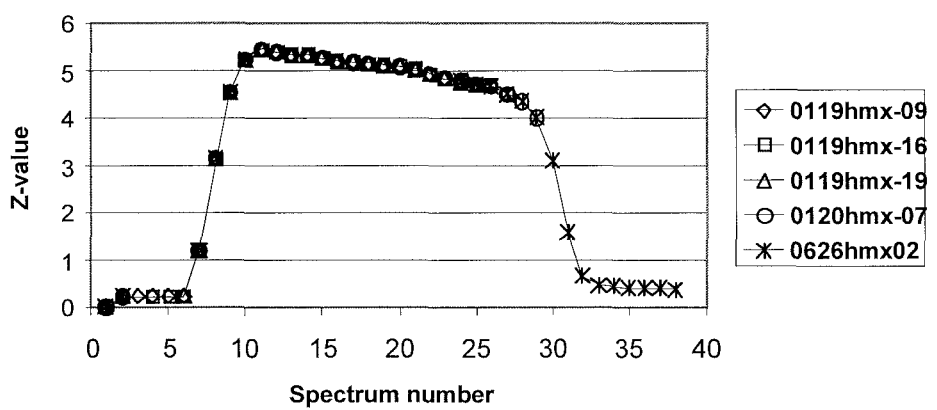
FIG. 6 is Z-characteristic plots of the idealized series of spectra, obtained from the HMX series of spectra of FIG. 5.
Figure 7:
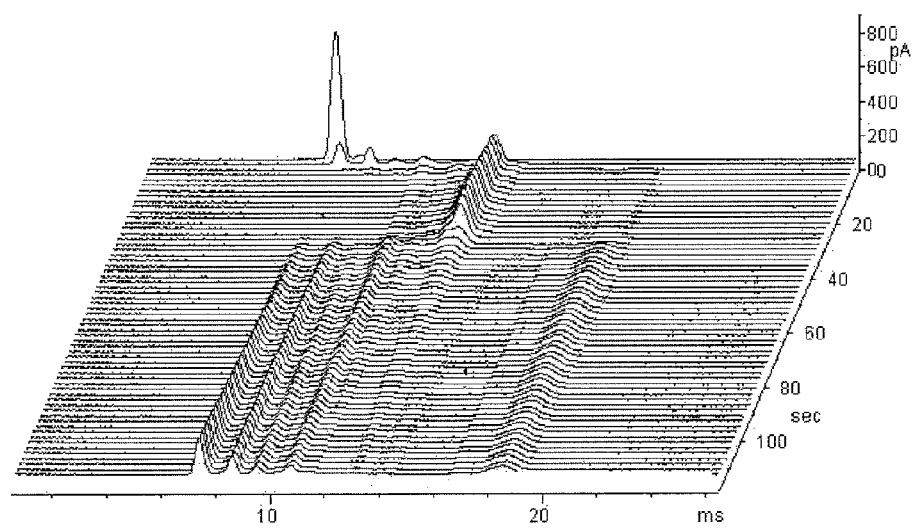
FIG. 7 is a series of spectra of the sample named "SPICE"
Figure 8:
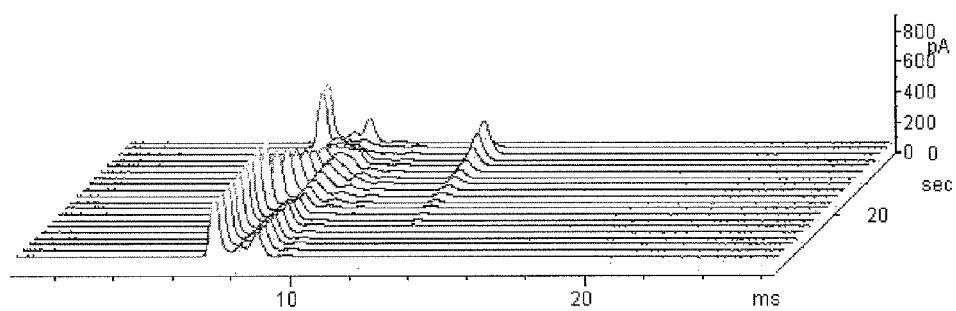
FIG. 8 is series of spectra of the explosive TNT.
Figure 9:
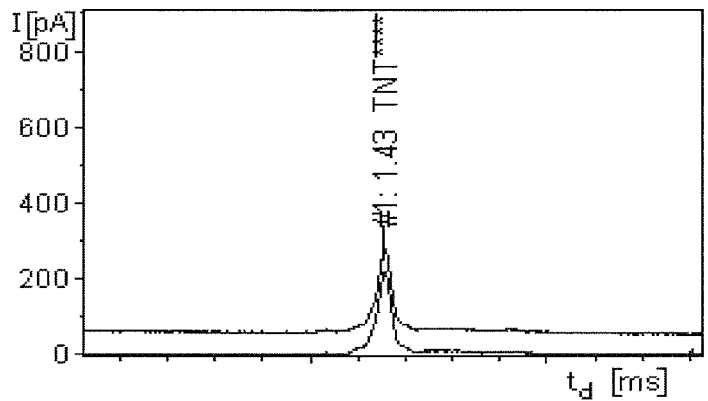
FIG. 9 are individual mobility spectra of TNT and SPICE showing that the spectra are almost identical.
Figure 10:
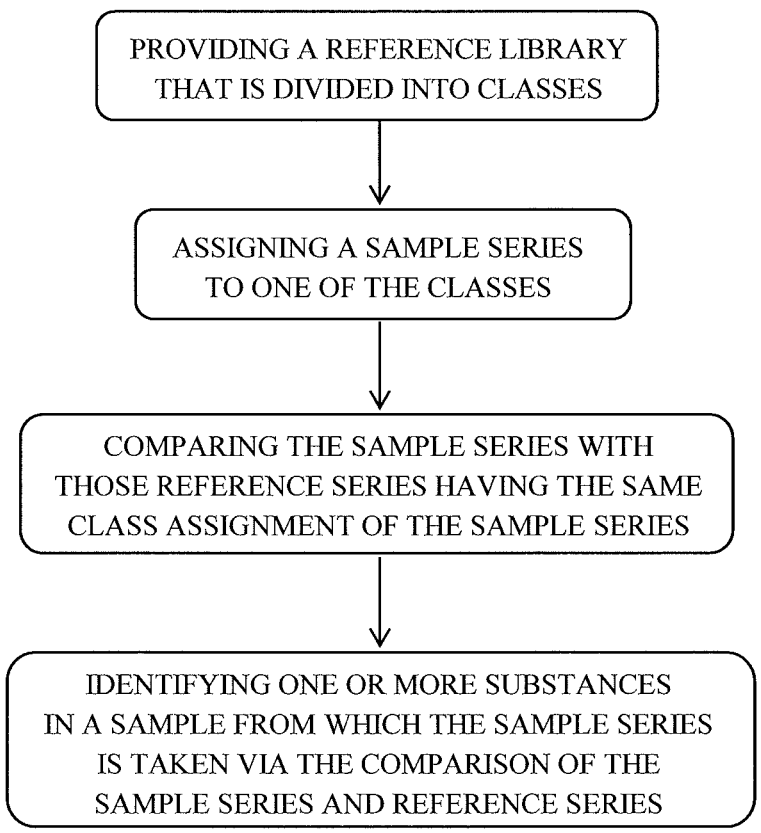
FIG. 10 is a flow chart illustration of processing steps to identify substances using similarity comparisons of sample series to reference series.

The computational effort required for the similarity comparisons may be reduced again by storing only one idealized series of spectra for each reference substance in any class of the reference library. The idealized series may be obtained from one or more real (measured) series of spectra of the reference substance in this class. The idealized series of spectra may, for example, be obtained by only including those mobility spectra which give a smooth curve for a characteristic, preferably a smooth curve for the spectrum center, i.e., of the Z-values. It is particularly advantageous to compose each idealized series of spectra from sections of the real series of spectra in this class. FIG. 6 shows the characteristic curves of the Z-values of such an idealized series of spectra. This idealized series of spectra was obtained from the real series of spectra of FIG. 5.

It has been found that, for many samples, the mobility spectra of certain Z-values in the ascending part of the Z-value curve do not agree with those of the same Z-values in the descending part, possibly due to adsorption and desorption processes during the sample introduction. The aim should therefore be to obtain a curve of the spectrum center from zero to the maximum value and back to zero, in order for mobility spectra in both the ascending and the descending part to be available for similarity comparisons. Then the similarity comparison between a series of ion mobility spectra of the analytical sample and series of ion mobility spectra of reference substances from one class of the reference library can preferably be carried out in such a way that mobility spectra in the respective series are compared which either have the same Z-value in the ascending curve or the same Z-value in the descending curve of the Z-values.

To ensure that this similarity comparison between the series of mobility spectra of the analytical sample and those of the reference sample is carried out with Z-values that are as similar as possible, it can be expedient to first compile a selected series of spectra for the analytical sample from the measured series of spectra, and a selected series of spectra for the reference sample from the idealized or real series of spectra stored in the reference library. The selected series of spectra no longer contain all the mobility spectra of the measured or idealized series of spectra, but only those which make a sufficiently strong contribution to the information content.

Some series of spectra, including some idealized series of reference spectra, have a wide plateau of mobility spectra with almost the same spectrum centers (Z-values) at the maximum, for example. These mobility spectra are usually also very similar to each other, so they all contain the same information. If these mobility spectra were all taken into account in the similarity comparison, the result would be a high weighting for these mobility spectra without increasing the information content. It can therefore be advantageous to include only one of these spectra in similarity comparisons during the selection process. This can, for example, be done by selecting only those spectra whose Z-values have a sufficiently large difference from the Z-value of the previously used spectrum for the similarity comparison.

In this selection of the mobility spectra for the similarity comparison, corresponding mobility spectra, each with Z-values that are as similar as possible, may be chosen for the selected series under analysis and for the selected reference series. It may happen, however, that for a mobility spectrum of the analytical sample, no suitable mobility spectrum with a sufficiently similar Z-value is available in the selected reference series. In this case a suitable mobility spectrum for the similarity comparison can be obtained by interpolation from adjacent mobility spectra of the series of spectra. Two, three or four adjacent mobility spectra with different Z-values can be used for this purpose. The interpolation can simply be done from peak to peak of the peak lists, but the mobility spectra of the idealized series of spectra must be so close together that adjacent mobility spectra also show the same peaks.

The similarity comparison of the two selected series of spectra for the analytical sample and the reference can then, in principle, be carried out one mobility spectrum at a time, or for the complete series of spectra in one go.

When determining a class of a series of spectra under analysis, it is possible that the characteristics $Z_{max}$ or $T_{max}$ used for the determination are not in the center of the class, but are located close to the edge of a class of the reference library. It may then be expedient to extend the similarity comparisons to the neighboring class as well.

The processing of data discussed above preferably run automatically as a computational program in a processor/computing device. An ion mobility spectrometer may store the computational program in its processor and, in particular, may include a storage unit comprising the reference library divided into classes.

What is claimed is:

1. A method for identifying substances in a sample, comprising:
    acquiring a sample series of ion mobility spectra of the sample using an ion mobility spectrometer;
    providing a reference library that is divided into classes with reference series, the assignment of each reference series to a class being determined from characteristics calculated from the ion mobility spectra of the reference series;
    determining the class assignment of the sample series from the characteristic calculated from the ion mobility spectra of the sample series; and
    comparing the sample series with those reference series having the class assignment of the sample series,
    where spectrum moments of the ion mobility spectra are used as characteristic, and where a curve of the spectrum moments along a sample axis is analyzed and coefficients of analysis are used as characteristics, where the spectrum moments include at least one of a first moment and a second moment, where the first moment is indicative of a spectrum center and the second moment is indicative of variance.

2. A method according to claim 1, where the sample series is compared with the reference series from a neighboring class if the sample series is located close to the boundary of its class.

3. A method according to claim 1, where a first spectrum moments and/or a second central spectrum moments along the series axis are used as characteristics.

4. A method according to claim 3, where a maximum value of the first spectrum moments and/or the second central spectrum moments along the sample axis is used as a characteristic.

5. A method according to claim 4, where a range of the maximum values over all the reference series is divided into intervals to provide classes for the corresponding characteristic.

6. A method according to claim 1, where the analysis is performed using at least one of (i) method of moments, (ii) Taylor expansion, (iii) Fourier transform and (iv) Wavelet transform.

7. A method for identifying substances in a sample, comprising:
    acquiring a sample series of ion mobility spectra of the sample using an ion mobility spectrometer;
    providing the reference library divided into classes with reference series, the assignment of each reference series to a class being determined from external measurement parameters; and
    assigning the sample series to one of the classes; and
    comparing the sample series only with the reference series having the same class assignment as the sample series,
    where spectrum moments of the ion mobility spectra are used as characteristic, and where a curve of the spectrum moments along the sample axis is analyzed and coefficients of the analysis are used as characteristics, where the spectrum moments include at least one of a first moment and a second moment, where the first moment is indicative of a spectrum center and the second moment is indicative of variance.

8. A method for identifying substances in a sample, comprising:
    acquiring a sample series of ion mobility spectra of the sample using an ion mobility spectrometer;
    providing the reference library divided into classes with reference series, the assignment of each reference series to a class being determined from external measurement parameters; and
    automatically assigning the sample series to one of the classes; and
    automatically comparing the sample series only with the reference series having the same class assignment as the sample series,
    where spectrum moments of the ion mobility spectra are used as characteristic, and where a curve of the spectrum moments along the sample axis is analyzed and coefficients of the analysis are used as characteristics, where the spectrum moments include at least one of a first moment and a second moment, where the first moment is indicative of a spectrum center and the second moment is indicative of variance.

* * * * *